(12) United States Patent
Hill et al.

(10) Patent No.: US 10,524,765 B2
(45) Date of Patent: Jan. 7, 2020

(54) REFINEMENT OF AN ANATOMICAL MODEL USING ULTRASOUND

(75) Inventors: Anthony D. Hill, Minneapolis, MN (US); D. Curtis Deno, Andover, MN (US); Martin M. Grasse, Boston, MA (US); Robert D. Aiken, Stillwater, MN (US); Daniel A. Feeney, Coon Rapids, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 12/979,170

(22) Filed: Dec. 27, 2010

(65) Prior Publication Data

US 2012/0165664 A1 Jun. 28, 2012

(51) Int. Cl.

| A61B 8/00 | (2006.01) |
| --- | --- |
| G06T 9/20 | (2006.01) |
| A61B 8/08 | (2006.01) |
| A61B 8/12 | (2006.01) |
| G06T 19/20 | (2011.01) |
| A61B 8/14 | (2006.01) |
| G16H 50/50 | (2018.01) |

(52) U.S. Cl.
CPC ............ *A61B 8/463* (2013.01); *A61B 8/0883* (2013.01); *A61B 8/12* (2013.01); *A61B 8/14* (2013.01); *A61B 8/4263* (2013.01); *A61B 8/483* (2013.01); *A61B 8/543* (2013.01); *G06T 9/20* (2013.01); *G06T 19/20* (2013.01); *A61B 8/4488* (2013.01); *G06T 2219/2012* (2013.01); *G16H 50/50* (2018.01)

(58) Field of Classification Search
USPC .................................. 600/437, 443, 450, 467
See application file for complete search history.

(56) References Cited

U.S. PATENT DOCUMENTS

| 6,106,466 | A | * | 8/2000 | Sheehan et al. .............. 600/443 |
| --- | --- | --- | --- | --- |
| 2003/0038802 | A1 | | 2/2003 | Johnson et al. |
| 2004/0101186 | A1 | * | 5/2004 | Tong ..................... G06T 7/0012 382/132 |
| 2007/0003137 | A1 | | 1/2007 | Cremers et al. |
| 2007/0223794 | A1 | * | 9/2007 | Preiss ....................... A61B 8/12 382/128 |
| 2007/0276226 | A1 | * | 11/2007 | Tal ........................ G06T 7/0026 600/424 |

(Continued)

FOREIGN PATENT DOCUMENTS

| EP | 2264670 | * 12/2010 |
| --- | --- | --- |
| WO | 2008/078265 | 7/2008 |

OTHER PUBLICATIONS

"International Search Report and Written Opinion", PCT/US2011/051443 dated Jan. 5, 2012.

(Continued)

*Primary Examiner* — Thomas J Hong
*Assistant Examiner* — Shahdeep Mohammed
(74) *Attorney, Agent, or Firm* — Dykema Gossett PLLC

(57) ABSTRACT

A method of refining an anatomical model includes acquiring a two-dimensional echocardiogram that has a variable intensity, relating the two-dimensional echocardiogram to a plurality of mapping points that exist in three-dimensional space, and determining a confidence value for each of two or more mapping points that corresponds to an intensity at a point on the two-dimensional echocardiogram.

20 Claims, 11 Drawing Sheets

(56) References Cited

U.S. PATENT DOCUMENTS

| | | | |
|---|---|---|---|
| 2008/0085042 A1 | 4/2008 | Trofimov et al. | |
| 2008/0101675 A1* | 5/2008 | Guiliguian | A61B 5/08 382/131 |
| 2008/0137927 A1 | 6/2008 | Altmann et al. | |
| 2009/0080738 A1* | 3/2009 | Zur et al. | 382/131 |
| 2009/0148012 A1 | 6/2009 | Altmann et al. | |
| 2010/0027861 A1* | 2/2010 | Shekhar et al. | 382/131 |
| 2010/0256493 A1 | 10/2010 | Chono | |
| 2011/0231162 A1* | 9/2011 | Ramamurthi | A61B 6/505 703/1 |

OTHER PUBLICATIONS

Supplementary European Search Report in EP Application No. 11853489.0 (dated Jun. 3, 2015).

* cited by examiner

REFINEMENT OF AN ANATOMICAL MODEL USING ULTRASOUND

CROSS-REFERENCE TO RELATED APPLICATION

This application is related to U.S. patent application Ser. No. 12/979,210, published as U.S. patent application publication no. 2012/0165672.

BACKGROUND OF THE INVENTION a. Field of the Invention

The present disclosure relates to catheter devices and systems, including devices and methods for refining an anatomical model using ultrasound.

b. Background Art

Electrophysiology (EP) catheters are used in connection with an ever-increasing number of procedures. Such catheters have been used, for example, for diagnostic, therapeutic, mapping, and ablative procedures. Catheters are commonly manipulated through a patient's vasculature to an intended site, for example a site within the patient's heart, and may carry one or more ultrasound transducers, position sensors, or electrodes for use in sensing, mapping, ablation, or diagnosis procedures.

BRIEF SUMMARY OF THE INVENTION

A method of refining an anatomical model includes acquiring a two-dimensional echocardiogram having a variable intensity; relating the two-dimensional echocardiogram to a plurality of mapping points existing in a three-dimensional model space; and determining a confidence value for a mapping point, where the confidence value corresponds to an intensity at a point on the two-dimensional echocardiogram.

The two-dimensional echocardiogram may be acquired from an ultrasound transducer associated with a distal portion of a catheter, and may be related to the plurality of mapping points using a sensed position and orientation of the ultrasound transducer. In an embodiment, the position and orientation of the transducer may be determined from a sensor associated with the distal end of the catheter.

In an embodiment, each mapping point may be displayed on a display device using a marker with a visual attribute that corresponds to the determined confidence value for that point. The visual attribute may be a color selected from a spectrum that corresponds to a range of confidence values, a symbol that represents a range of confidence values, or some other similar indicator.

In an embodiment, a plurality of mapping points may define a three-dimensional model within the three-dimensional model space. The system may be configured to compare the confidence value of a mapping point not part of the model to a threshold, and include it into the model if the confidence value of the point is above the threshold.

In an embodiment, the system may use the two-dimensional echocardiogram to generate a three-dimensional echocardiogram intensity model within the three-dimensional model space. The three-dimensional echocardiogram intensity model may comprises a plurality of voxels, where each voxel may have an intensity value that relates to an intensity of a portion of one or more acquired two-dimensional echocardiograms. The three-dimensional echocardiogram intensity model may be updated to include successively acquired two-dimensional echocardiogram information. In an embodiment, the update may occur according to a Bayesian inference algorithm.

DETAILED DESCRIPTION OF THE INVENTION

Figure 1:
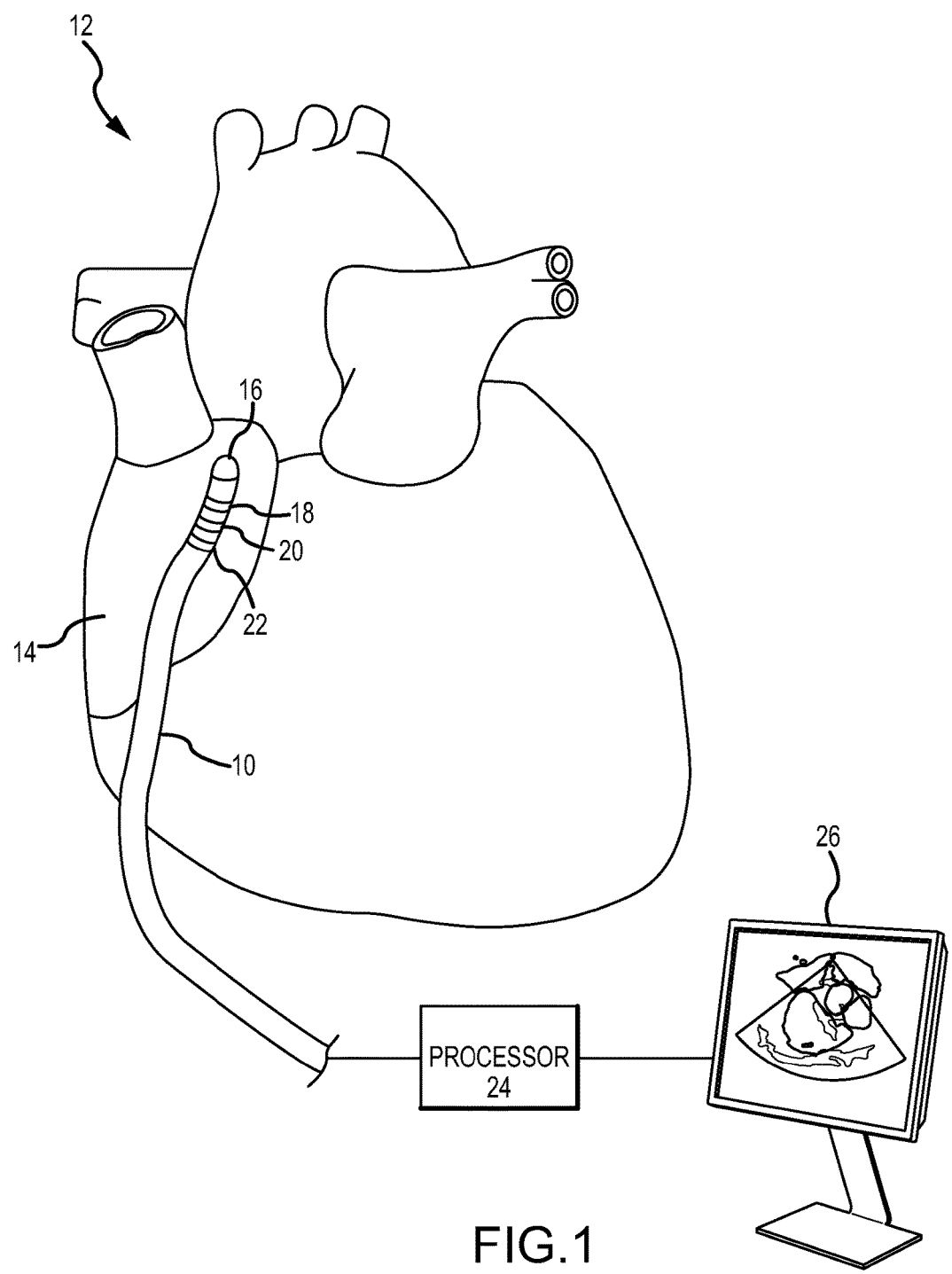
FIG. 1 is a general representation of a cardiac anatomy together with a catheter.

Referring to the drawings, wherein like reference numerals are used to identify like or identical components in the various views, FIG. 1 generally illustrates a catheter 10 positioned within a portion of a cardiac anatomy 12. As generally illustrated in FIG. 1, the catheter 10 may, for example, be positioned within the right atrium 14 of the cardiac anatomy 12. In an embodiment, the catheter 10 may be an intracardiac echo (ICE) catheter that may include one or more ultrasound transducers, such as ultrasound transducer 16. The catheter 10 may further include one or more position detectors 18, 20, 22, which may be located toward its distal end, and configured to provide a signal indicative of both a position and orientation of a portion of the catheter 10.

In an embodiment, the position detectors 18, 20, 22, may comprise electrodes (e.g., ring-type or spot type or partially masked electrodes) configured to be responsive to an electric field transmitted within the body of the subject. Such electrodes may be used to sense an impedance at a particular location and transmit a representative signal to an external computer or processor. An example of an impedance-based position detection system is the EnSite NavX™ system, commercialized by St. Jude Medical, Inc. of St. Paul, Minn., and described in U.S. Pat. No. 7,263,397, entitled "Method And Apparatus For Catheter Navigation And Location And Mapping In The Heart," which is incorporated herein by reference in its entirety.

In an embodiment, the position detectors 18, 20, 22 may comprise metallic coils located on or within the catheter 10, and may be configured to be responsive to a magnetic field transmitted through the body of the subject. Such coils may, for example, sense the strength of the field at a particular location and transmit a representative signal to an external computer or processor. An example of a magnetic-based position detection system is the Medical Positioning System (gMPS) for navigation developed by St. Jude Medical, Inc. through its MediGuide Inc. business unit of Haifa, Israel, and generally shown and described in U.S. Pat. No. 7,386,339 entitled "Medical Imaging and Navigation System," which is incorporated herein by reference in its entirety.

The ultrasound transducer 16 may be configured to project an ultrasound signal outward through adjoining tissue and/or fluid, and may further receive an ultrasound echo from such tissue or fluid. In an embodiment, the ultrasound transducer 16 may comprise a unidirectional phased array ultrasound transducer. Such a transducer may be configured to project ultrasound energy from one side of the catheter in a two dimensional plane generally aligned with the longitudinal axis of the catheter. In another embodiment, the ultrasound transducer 16 may be a radially scanning ultrasound transducer that is configured to project ultrasound energy radially outward from the catheter and may be further configured to rotate about the circumference of the catheter (e.g., through 360 degrees).

The system may additionally include a processor 24 and a display device 26. The processor, among other things, may be configured to receive position and/or orientation signals from one or more position sensors associated with the distal end portion of the catheter (e.g., position sensors 18, 20, 22), may receive ultrasound information from one or more ultrasound transducers (e.g., ultrasound transducer 16), may include and/or maintain a three-dimensional volumetric model of the cardiac anatomy, and may provide various displays to a display device 26.

Figure 2:
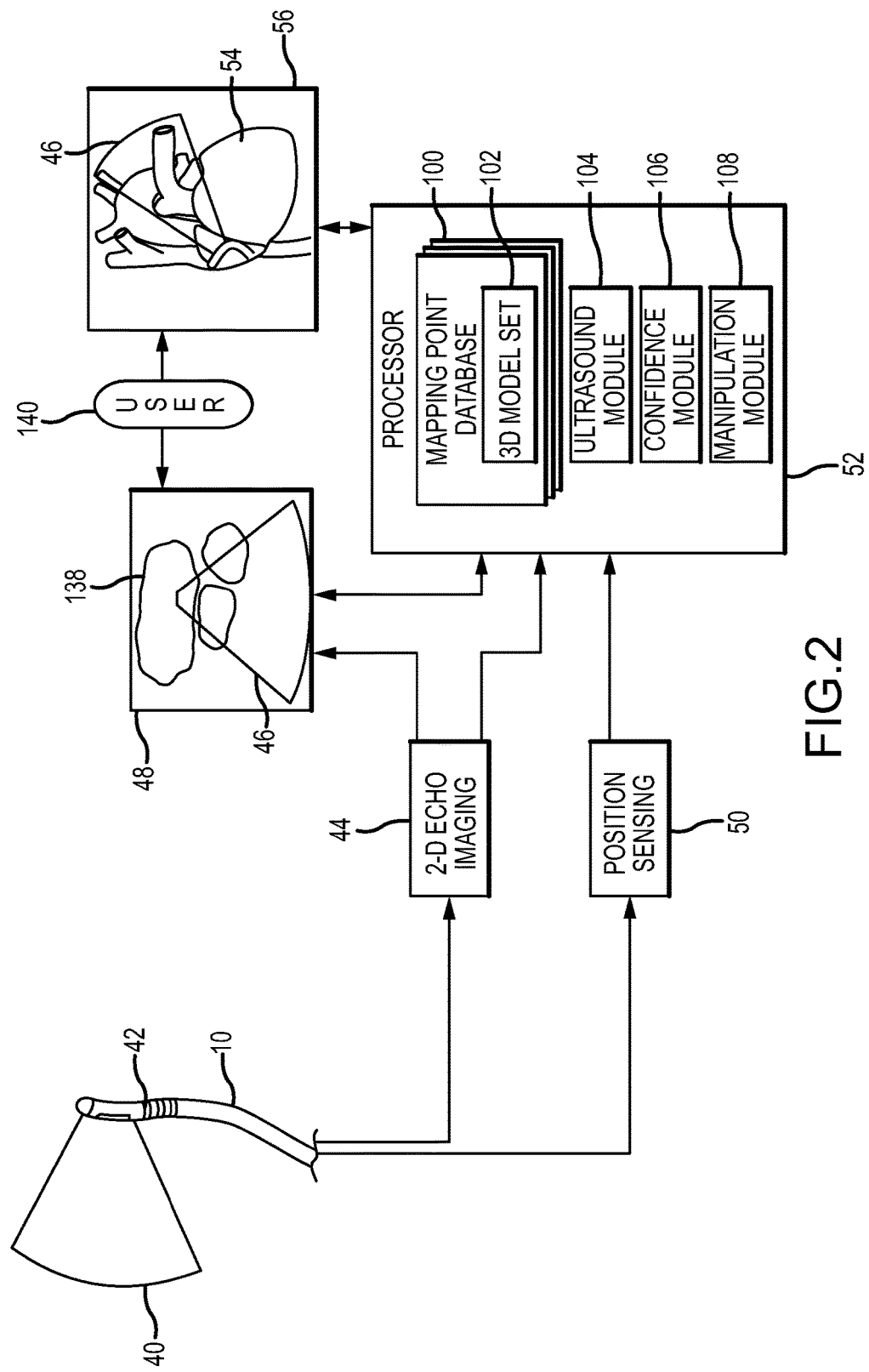
FIG. 2 is a schematic functional diagram illustrating a system for refining an anatomical model using ultrasound.

FIG. 2 generally illustrates a schematic representation of a system for refining an anatomical model. As shown, the system may include a catheter 10, such as an ICE catheter, that is capable of projecting and receiving ultrasound information 40. The ultrasound information 40 may be transmitted/received using, for example, a phased array ultrasound transducer or a radially scanning ultrasound transducer. A distal portion of the catheter 10 may further include one or more position sensors 42 that are configured to receive an external signal, from which a position and orientation may be derived. The one or more position sensors may include, for example, electrodes configured to monitor an externally generated electric field, such as with the EnSite NavX™ system, or may include magnetically responsive coils configured to monitor an externally generated magnetic field, such as with the Medical Positioning System (gMPS).

In an embodiment, the catheter 10 may provide ultrasound information 40 to a 2-D echo imaging system 44. The echo imaging system 44 may convert the received ultrasound information into an ultrasound image 46, which may be displayed on a monitor 48.

The catheter 10, may additionally provide a signal from each of one or more position sensors 42 to a position sensing system 50. From the signal, the position sensing system 50 may derive a position and orientation of the distal portion of the catheter 10. The position and orientation can have up to six degrees of freedom, depending upon the number and type of sensors and the type of system employed. In an embodiment, the derived 3D position and orientation may be provided to a processor 52 and may be logged as a mapping point, or may be used to establish or locate the ultrasound information 46 or a transducer in three dimensional space.

The processor 52 may maintain a collection of mapping points within a mapping point database 100. In an embodiment, each mapping point (P) within the mapping point database 100 may be physically defined in three dimensions (e.g., in a Cartesian space). Mapping points may be represented, for example, by an array as shown in Equation 1, where (x, y, z) represent the location of a point in three dimensions. Furthermore, each mapping point may comprise one or more additional parameters (e.g., ($C_1$, $C_2$, ..., $C_n$)) that represent sensed information acquired by the catheter 10 at that particular location.

$$P=[x,y,z,C_1,C_2,\ldots,C_n] \quad \text{Eq. 1}$$

In an embodiment, each mapping point may represent a previous location of a catheter 10, as recorded by a position sensing system 50. However, in another embodiment, the mapping points may be imported into the database from an external source, and/or may be automatically generated by the system. This collection of mapping points (i.e. the "point cloud") may provide a basis for a three-dimensional anatomical model 54 of the subject's actual cardiac anatomy 12.

In an embodiment, a three-dimensional anatomical model 54 may be constructed from the point cloud by identifying or skinning a set of the points 102 within the database 100 that are likely to represent the subject's cardiac anatomy. In a simplified and exemplary embodiment, the skin may be constructed from a plurality of shell-type elements that generally overlay or represent the outermost points of the point cloud. Other sophisticated techniques for creating such models are taught in U.S. Pat. No. 7,670,297, entitled "Chamber Mapping System;" U.S. Pat. No. 7,263,397, entitled "Method and Apparatus for Catheter Navigation and Location and Mapping in the Heart," and in U.S. Patent Publication No. 2008-0221643 (application Ser. No. 11/715,919), entitled "System and Method for Correction of Inhomogeneous Fields," which are all herein incorporated by reference in their entirety. Once a shell model has been constructed from the collection of mapping points 100, the processor 52 may display a representation of the model 54 on a model display 56.

As further illustrated in FIG. 2, the processor 52 may include an Ultrasound Module 104 that is configured to receive a representation of the ultrasound echo image 46 and relate the representation to the collection of mapping points. The processor 52 may also include a Confidence Module 106 that may determine a relative measure of "confidence" or "trustworthiness" for each mapping point. In an embodiment, this measure of confidence may be based on the amount of corroborating information provided by an ultrasound image, and may be used to provide a measure of certainty as to whether a recorded mapping point lies on a tissue boundary. Furthermore, the processor 52 may include a Manipulation Module 108 that may alter a visual attribute of a displayed mapping point based on a measure of confidence, and/or may automatically manipulate the shelled model to only include mapping points with a certain minimum measure of confidence. For purposes of this description, each functional "module" has been illustrated separately from the other modules, however, this should not be interpreted to reflect or require a particular software configuration or organization. Furthermore, it is contemplated that there may be overlap or dependencies between the various modules when implemented. Each module will be described is greater detail below.

Figure 3:
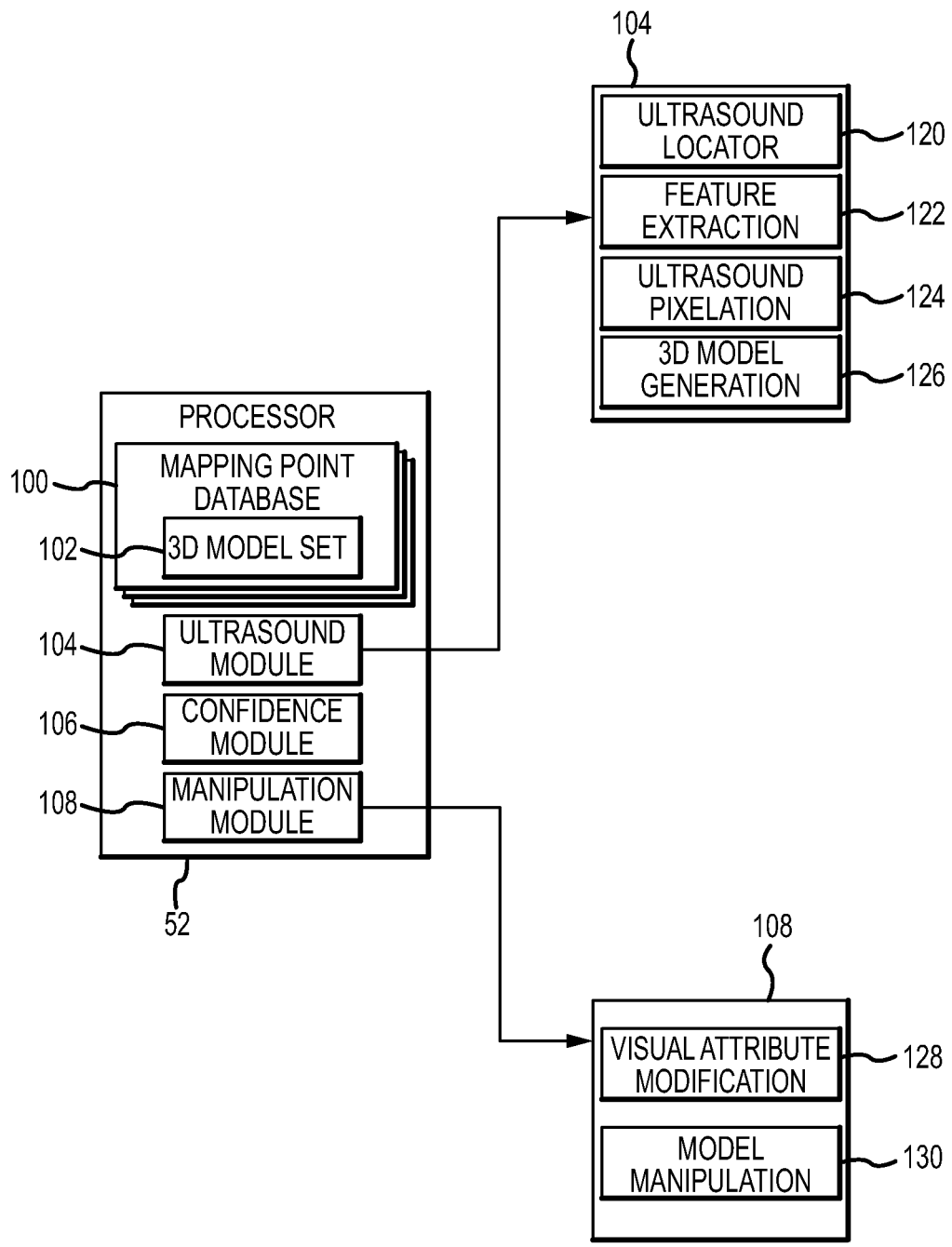
FIG. 3 is a further functional representation of features associated with a processor such as shown in FIG. 2.

FIG. 3 is a further refined diagrammatic illustration of various modules of an embodiment of a processor, such as the processor 52 generally illustrated in FIG. 2. As shown, the ultrasound module 104 and manipulation module 106 may each include one or more sub-modules or sub-functions. In an embodiment, the Ultrasound Module 104 may include an Ultrasound Locator sub-module 120 that is configured to locate two-dimensional ultrasound information 40 within 3D model space.

Figure 4:
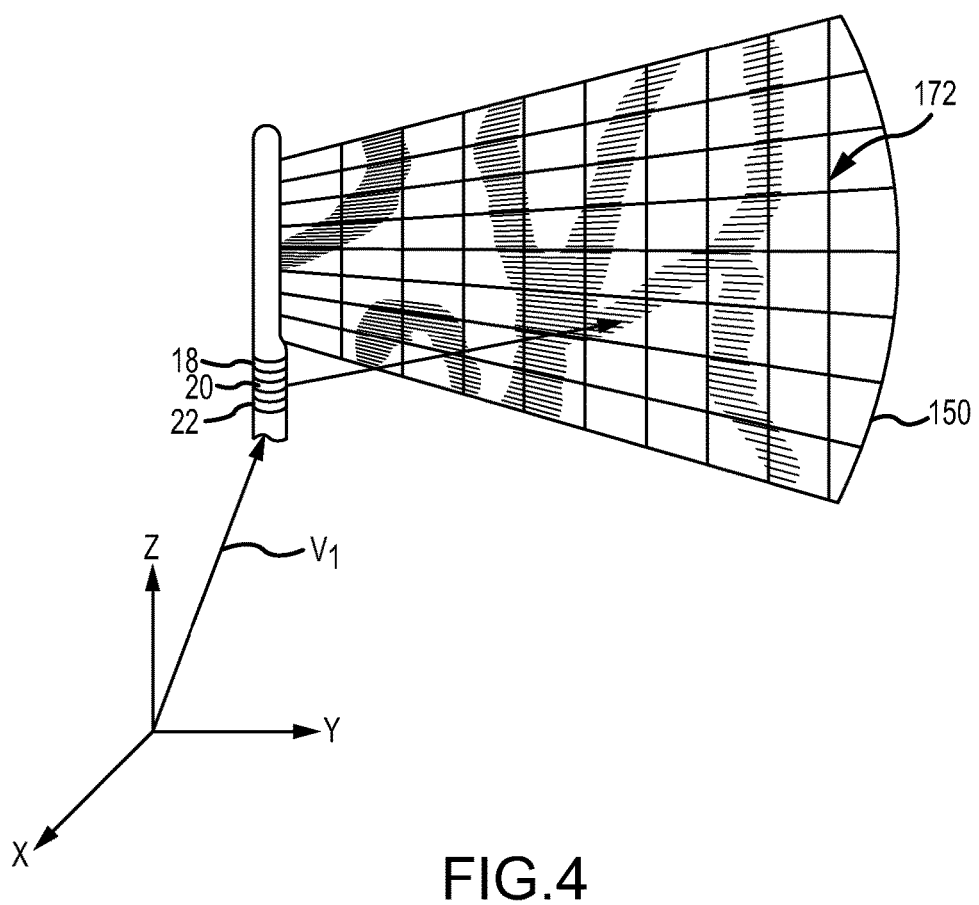
FIG. 4 is an illustration of a catheter projecting ultrasound.

As generally illustrated in FIG. 4, the Ultrasound Locator module 120 may use the position and orientation of the catheter ($V_1$) (as provided by a positioning system 50), together with a knowledge of the physical relationship between position sensors (e.g., sensors 18, 20, 22) and the ultrasound spread 150, to locate the ultrasound 150 in three dimensional model space. After the two-dimensional ultrasound information 150 is located within the model space, the processor 52 may display it together with the three-dimensional anatomical model 54 and any associated mapping points, as generally shown in FIG. 5a.

Referring again to FIG. 3, the Ultrasound Module 104 may further include a Feature Extraction sub-module 122 that may use a sensed position and orientation of the ultrasound information 150 to extract features from the three-dimensional anatomical model 54 that lie within a given tolerance of the 2D ultrasound plane. This concept is generally illustrated with general reference to FIGS. 5a and 5b.

The Extraction sub-module 122 may generally define a 2D model slice plane that exists within the 3D model space and contains ultrasound information 150. This slice plane may be used as a cutting plane for the purpose of extracting features from the model. In an embodiment, the intersection of the model slice plane and cardiac model 54 may create a set of boundary lines that represent the walls of a cardiac anatomy within that plane. As shown generally in FIG. 5b, once extracted, the boundary information 152 may then be overlaid on an independent visualization of the ultrasound information 154 to create an augmented echo image 156. Likewise, mapping points that exist within a given tolerance of the model slice plane may be extracted and, if desired, displayed within the augmented echo image 154.

Figure 5A:
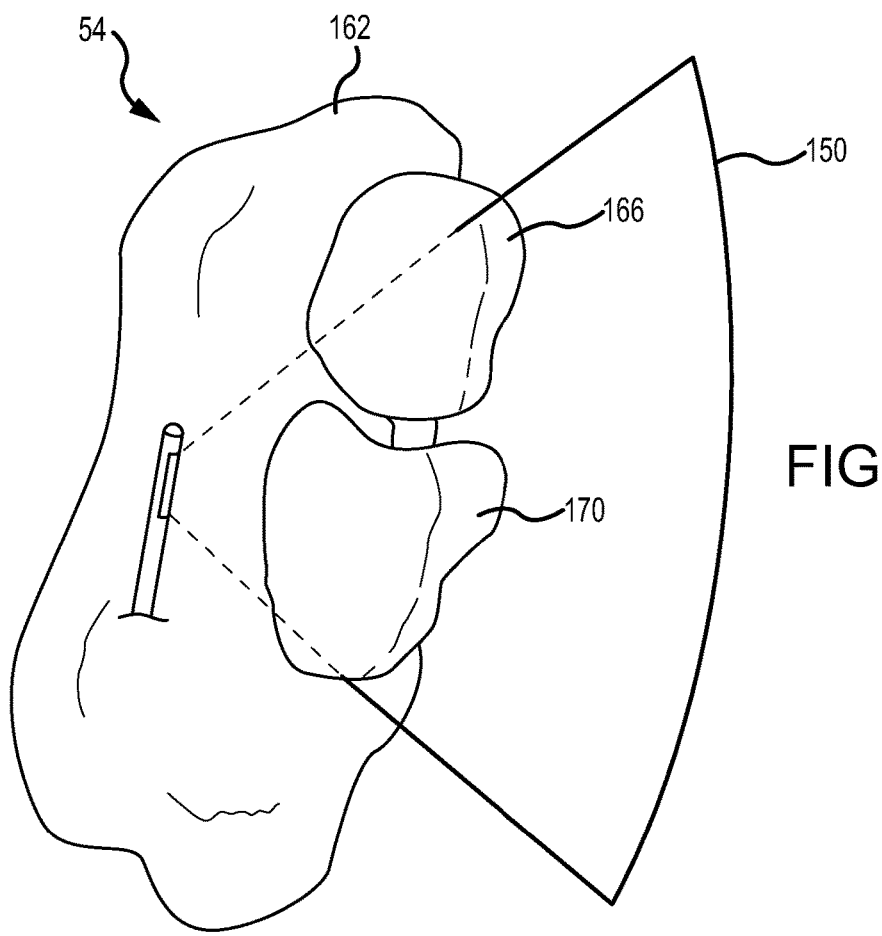
FIG. 5a is a general representation of a volumetric cardiac model including a representation of a phased array catheter.
Figure 5B:
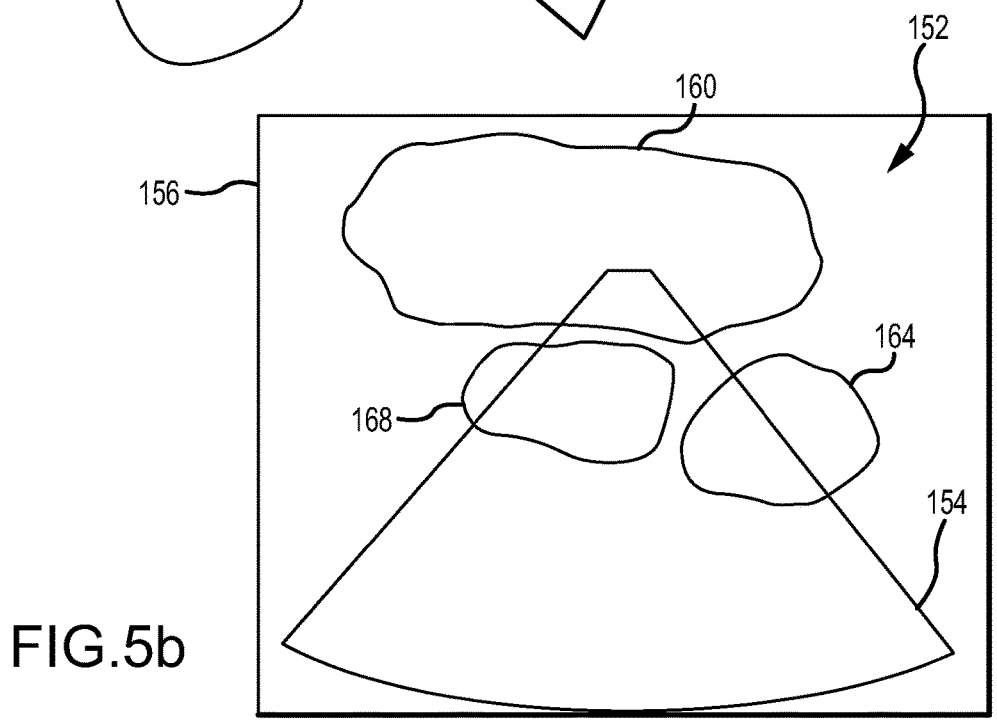
FIG. 5b is a general representation of an augmented echo image including a phased array ultrasound image and including boundary information.

In the exemplary illustration shown in FIGS. 5a and 5b, the augmented echo image 156 may contain a first boundary marker 160 that corresponds to structure 162 depicted in FIG. 5a. Likewise a second boundary marker 164 may correspond to structure 166, and a third boundary marker 168 may correspond to structure 170.

The Ultrasound Module 104 may further include an Ultrasound Pixelation sub-module 124 that may analyze a visualization of the ultrasound information 150, deconstruct it into a plurality of pixels, and assign each pixel a representative image intensity corresponding to sensed ultrasound reflectivity. FIG. 4 illustrates an exemplary pixel subdivision, where the ultrasound spread has been initially divided into a plurality of regularly shaped pixels (e.g., pixel 172). In practice, a pixel resolution may be on the order of 320 to 640 pixels per inch; however, the density may be more or less depending on the speed and memory constraints of the processor 52. Once the image has been subdivided into the plurality of image pixels, each pixel may then be assigned an intensity value corresponding to the average perceived image intensity across that pixel. In an embodiment, the intensity value for each pixel may be a numeric value.

Figure 6:
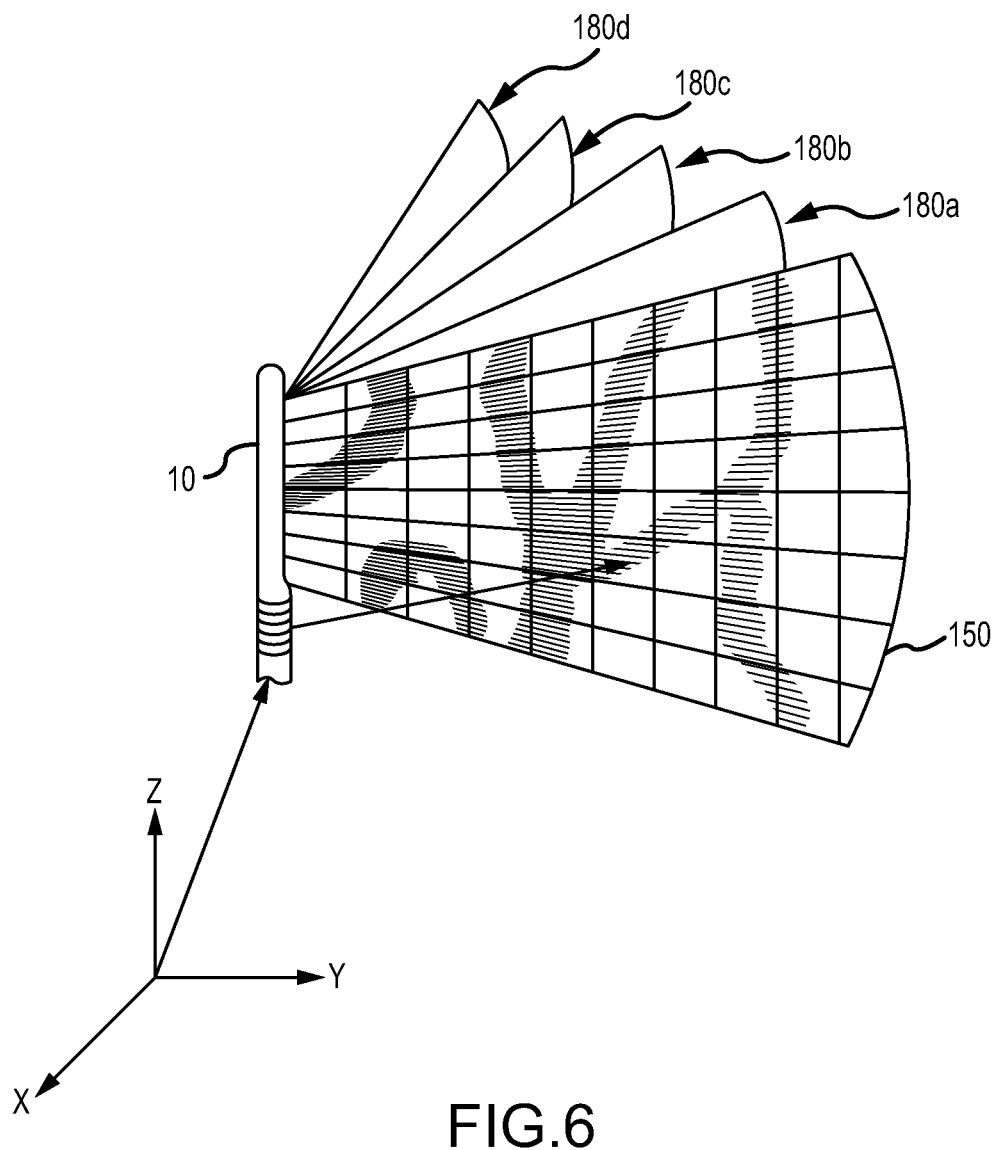
FIG. 6 is an illustration of a catheter such as shown in FIG. 4, generally demonstrating ultrasound being swept around a longitudinal axis of the catheter.

Finally, the Ultrasound Module 104 may include a 3D Model Generator 126. As shown in FIG. 6, during a procedure, the catheter 10 may be manipulated in a manner that causes the ultrasound spread 150 to take a plurality of different positions and orientations. For example, simply rotating the catheter may cause the ultrasound spread 150 to assume poses 180a, 180b, 180c, 180d. Similarly, the catheter may be translated, or deflected away from its longitudinal axis to further manipulate the ultrasound.

Figure 7:
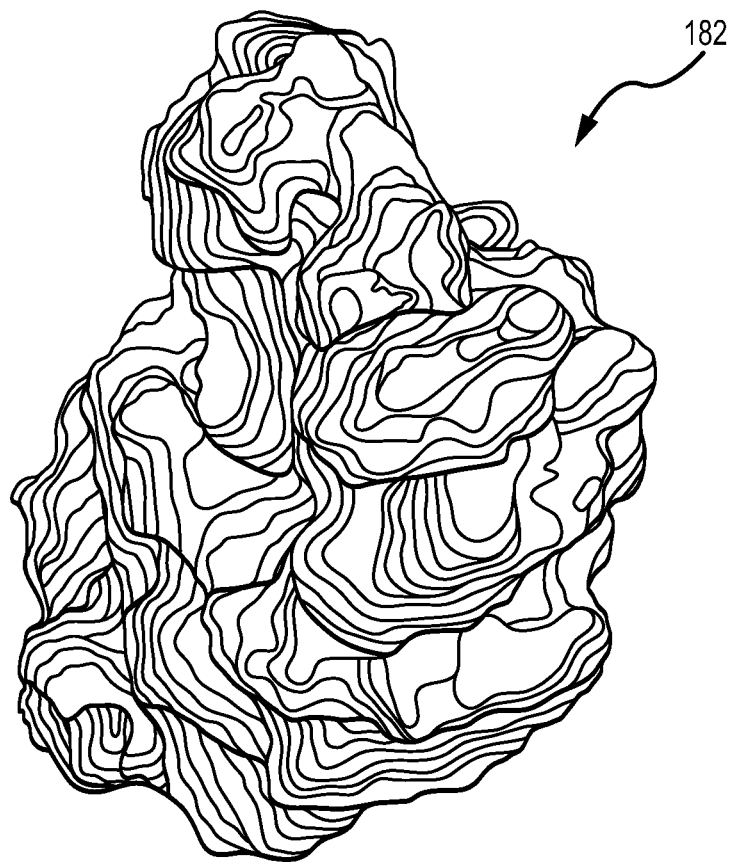
FIG. 7 is an illustration of a voxel model of a chamber of a subject's cardiac anatomy.

At each pose, pixels within the visualization may be spatially located in three-dimensional space. Knowing these locations, the Model Generator 126 may then map associated pixel intensities to corresponding positions within a three-dimensional volume. Each intensity within the 3D space may be represented as a volumetric pixel (voxel), such as a cubic element, that has a corresponding intensity. This mapping may then result in a three-dimensional intensity map that is assembled from the various slice data. As successive ultrasound poses are recorded and associated to the 3D space, the model may be successively updated, for example, by using a Bayesian Inference Algorithm. By setting or providing an appropriate intensity threshold, the Model Generator 126 may effectively "hide" portions of the volume that exhibit an ultrasound reflection intensity below the threshold. As illustrated in FIG. 7, the resulting unhidden portion of the volume may be viewed as a voxel model 182 that represents a cardiac structure (or other objects exhibiting a comparatively high ultrasound reflectivity (e.g., foreign objects)).

Referring again to FIG. 3, the processor 52 may include a Confidence Module 106 that may determine a relative measure of "confidence" or "trustworthiness" for each mapping point within the mapping point database 100. In an embodiment, the measure of confidence or trustworthiness may be greater for mapping points that are confirmed to be immediately adjacent an actual tissue boundary, and lesser for mapping points that are more interior to the chamber.

Figure 8:
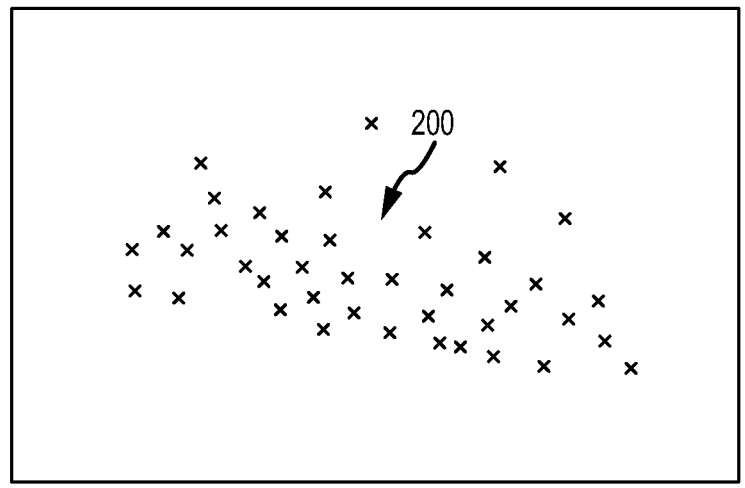
FIG. 8 is a two-dimensional subset of a mapping point cloud.

FIG. 8 illustrates an exemplary portion of a mapping point cloud 200. As generally described above, each mapping point, represented by an "x" is registered in the mapping point database 100 as a three-dimensional location. The illustrated mapping points 200 represent an extracted subset of points from the database that may lie in, or may be proximate to a two-dimensional plane. Without further evidence, each displayed mapping point may be substantially similar to all other displayed mapping points. In an embodiment, the Confidence Module 106 may examine each mapping point in light of other available information or evidence to aid the system in determining which points are more likely to represent a tissue boundary. An example of evidence that may be used to provide a measure of confidence may be the ultrasound information obtained from an intracardiac echo catheter.

Figure 9:
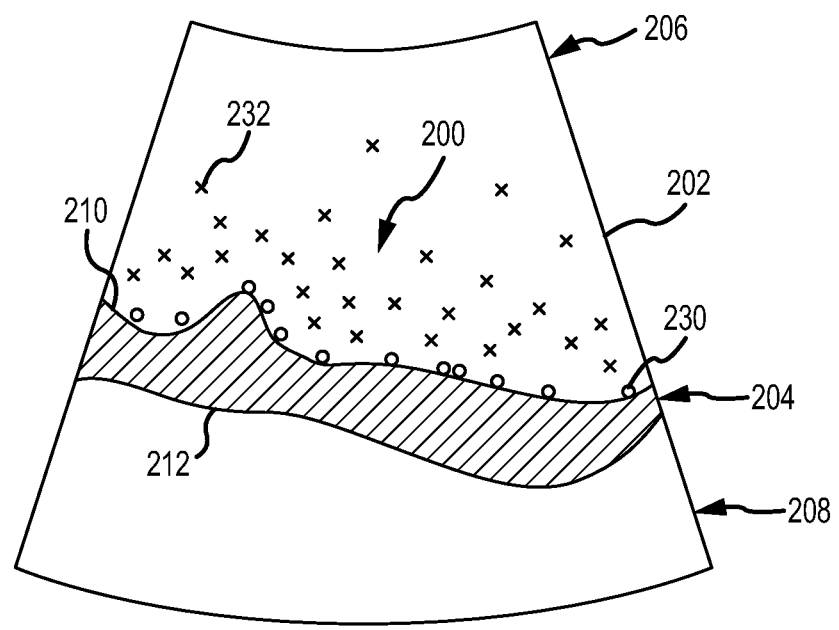
FIG. 9 illustrates the mapping points of FIG. 8, generally overlaid on an ultrasound image.

As shown in FIG. 9, a planar collection of mapping points, such as illustrated in FIG. 8, may be overlaid on an ultrasound image 202 captured from the same spatial plane as the points 200. Prior to a confidence evaluation, the ultrasound image 202 may be pixilated using known or herein described methods. In an embodiment, the Confidence Module 106 may analyze the pixilated ultrasound image to determine an intensity gradient over the image. This analysis may involve numerical methods, such as, for example, by calculating the difference in intensity values between adjacent pixels or groups of pixels. The existence of a gradient that is above (or below) a given threshold may signify a transition between fluid or tissue with a low ultrasound reflectivity and fluid or tissue with a higher reflectivity. Such a transition may detect boundaries between blood (i.e., lower reflectivity) and cardiac tissue (i.e., higher reflectivity). For example, within the exemplary ultrasound image 202 illustrated in FIG. 9, there may be one or more areas of high ultrasound reflectivity 204 that may represent a portion of the cardiac wall. Adjacent these high-intensity areas, there may be areas of lesser intensity (e.g. areas 206, 208) that may represent cavities in or near the cardiac anatomy 204. For example, region 206 may represent an area inside the cardiac chamber, and area 208 may represent an area outside the cardiac chamber. The intensity gradient would likely be the highest at the transitions between area 204 and areas 206, 208 (i.e., respectively, at boundaries 210, 212)

Once tissue boundaries have been identified, a measure of confidence may be assigned to each mapping point based on its proximity to the boundary. In an embodiment, the confidence value may be based on a point's absolute proximity to the boundary. For example, mapping points more proximate to the perceived tissue boundary may be assigned a higher confidence value than points more distal to the boundary. While FIG. 9 illustrates an overlay of mapping points on the ultrasound in a two-dimensional construct, the mapping point overlay and/or assignment of confidence values may likewise be performed in three dimensions, such as with an ultrasound model as generally shown in FIG. 7.

The Confidence Module 106 may additionally be capable of identifying anomalies or abnormalities in an ultrasound image by examining the magnitude of the ultrasound intensity. In an embodiment, if an abnormality is detected, the Confidence Module 106 may lower the corresponding confidence of proximate mapping points. For example, a high-intensity plateau in the intensity map, may indicate the presence of a metallic object that is reverberating. Similarly, a low-intensity plateau in the intensity map may indicate a highly echogenic object that does not transmit sound deeper. In either circumstance, the system may decrease the confidence of any points immediately proximate the plateau, such as for points that may lie in ultrasound darkness due to a object.

Finally, referring again to FIG. 3, the Manipulation Module 108 may include a Visual Attribute Modification Module 128 that may modify one or more visual attributes of overlaid mapping points based on an associated degree of confidence. Additionally, Manipulation Module 108 may include a Model Manipulation Module 130, that may directly manipulate the skinned model based on the various confidence measures.

As illustrated in FIG. 9, the processor 52 may alter the appearance of one or more mapping points 200 based on a mapping point's confidence value. In an embodiment, the processor may use symbols to represent each mapping point, where the symbol is chosen to represent, for example, a range of confidence values. In an exemplary embodiment, the system may display mapping points with a confidence value above a particular threshold (i.e. an upper range) as an "o" (e.g., mapping point 230). Likewise, mapping points having a confidence value below the threshold may be displayed as an "x" (e.g., mapping point 232). In another embodiment, the processor 52 may display each mapping point using a color that may be selected from a spectrum corresponding to a range of confidence values. As may be appreciated, various other designators or identifiers may be used to provide an indication of the confidence value assigned to a mapping point.

Figure 10A:
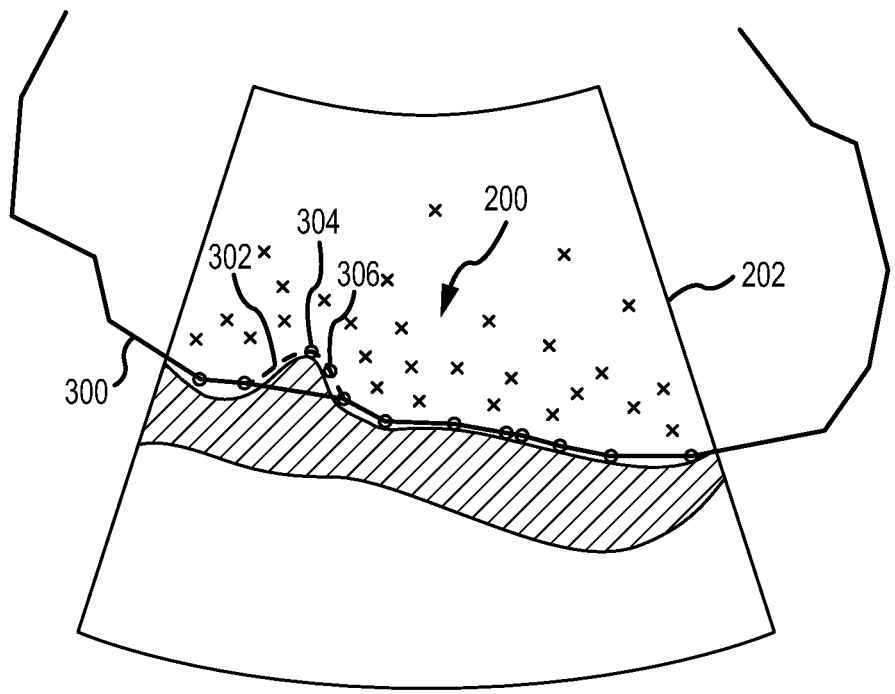
FIG. 10a is the illustration of FIG. 9, with model boundary information generally included
Figure 10B:
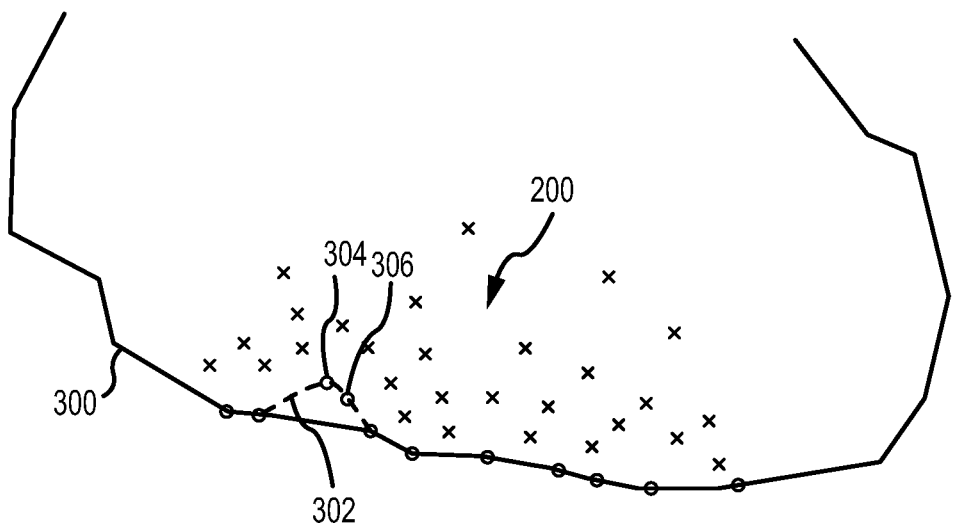
FIG. 10b is the illustration of FIG. 10a with the ultrasound image removed.

The Manipulation Module 108 may also be capable of manipulating a skinned model to include mapping points that have been assigned a sufficiently high confidence value. Similarly, if a given model set 102 includes mapping points that do not meet a particular confidence threshold, the system may exclude them from the model. In an exemplary embodiment, as shown in FIGS. 10a and 10b, an existing model 300 can be constructed by skinning the outermost points of the point cloud (note that mapping points outside of the ultrasound image 202 are not illustrated). The augmented ultrasound image in FIG. 10a illustrates that the model 300 that bisects a portion of the cardiac tissue, and is therefore inaccurate. Following the confidence evaluation, a corrected model 302 may be generated that specifically incorporates more interior mapping points 304 and 306. FIG. 10b illustrates the model 300 and corrected model 302 without the visual benefit of the ultrasound image 200.

In an embodiment, the Model Manipulation Module 130 may be configured to automatically adjust the 3D Model Set 102 (and corresponding skinned model) based on the mapping point confidence evaluation. In another embodiment, the system may present a visualization of the augmented ultrasound image to a user (similar to FIG. 9 or 10a), and allow the user to manually adjust the model 300 at his/her discretion. In an embodiment, if a change is made to the model set 102 in one two-dimensional plane, the manipulation module 130 may be configured to make any necessary adjustments in adjacent planes to ensure the three dimensional continuity of the model surface.

Figure 11:
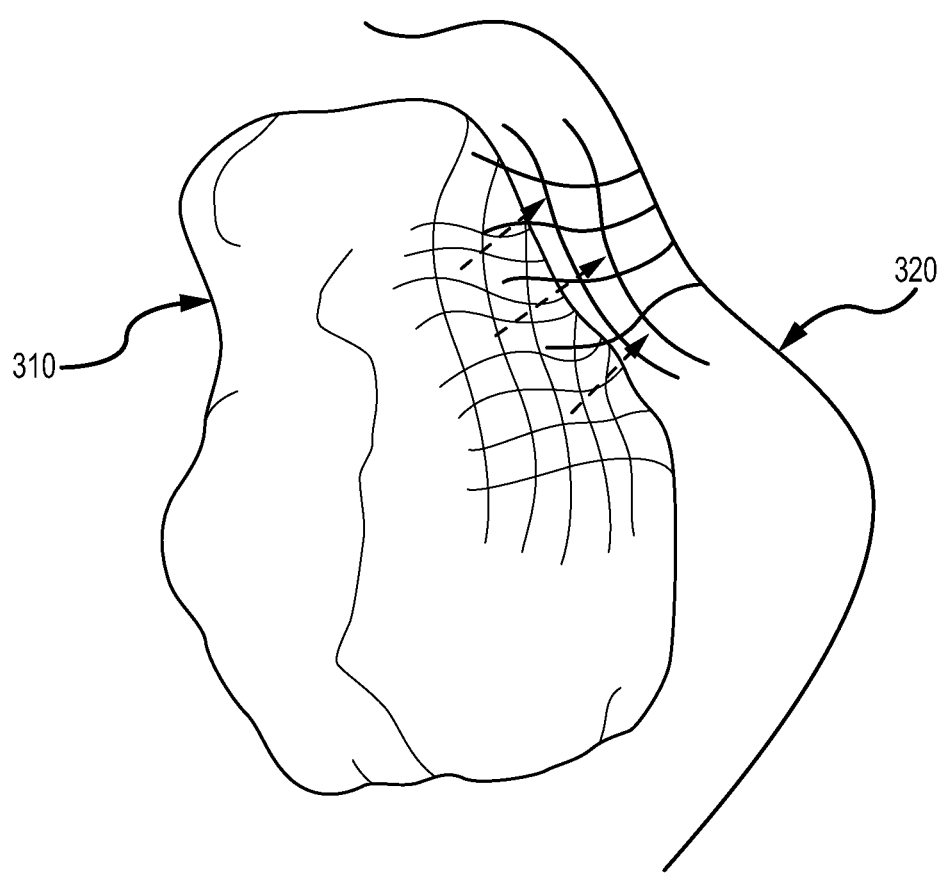
FIG. 11 is a general illustration of a skinned model adjusted in three-dimensional space in view of a voxel-based ultrasound model.

While FIGS. 10a and 10b illustrate the model correction in a two-dimensional context, as generally illustrated in FIG. 11, the correction may also be performed in three dimensions. In an embodiment, prior to a confidence evaluation, a three-dimensional mapping point (e.g., NavX) model 310 may be globally scaled, rotated, and/or translated to best align with a three-dimensional ultrasound model 320 (of the type illustrated in FIG. 7). Once a best fit is obtained, the adjusted model set, along with interior mapping points, may be evaluated to determine the degree of confidence for each point.

Figure 12A:
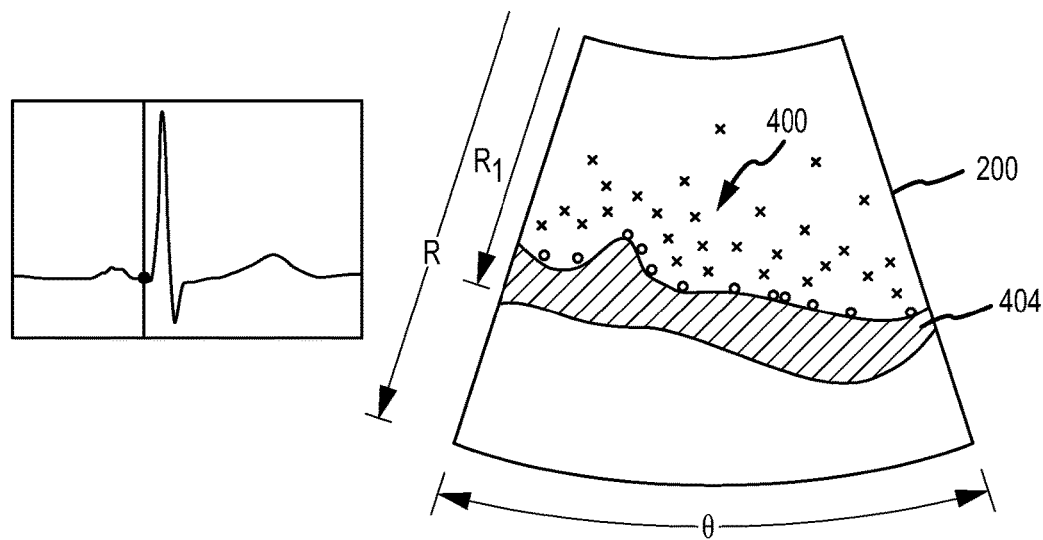
FIG. 12a is a general illustration of an ultrasound image and overlaid mapping point cloud keyed to a first phase of an anatomical rhythm.
Figure 12B:
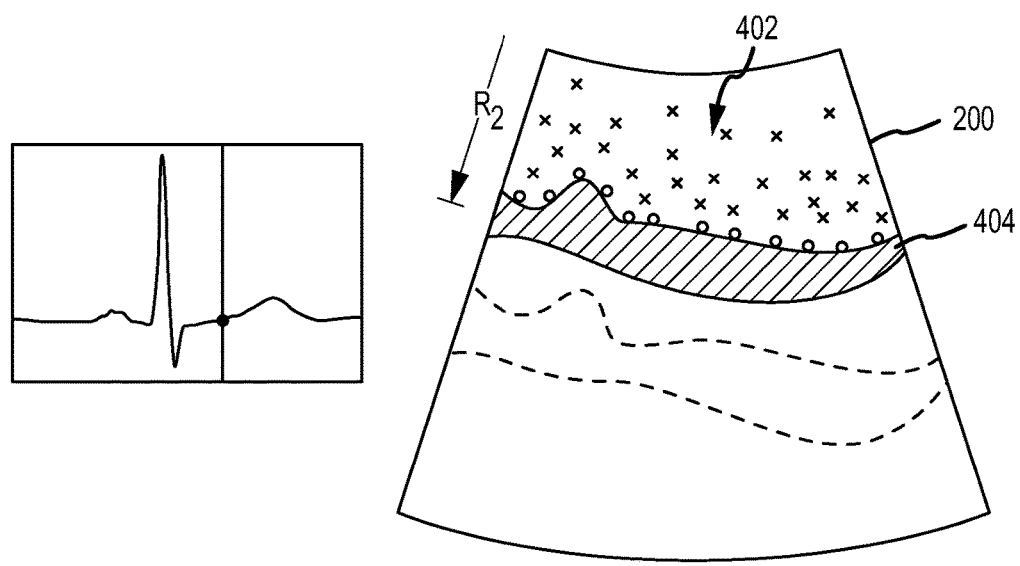
FIG. 12b is a general illustration of an ultrasound image and overlaid mapping point cloud keyed to a second phase of an anatomical rhythm.

In an embodiment, the mapping points may be discretely recorded and/or adjusted to account for one or more external factors, such as, for example, cardiac rhythm or patient breathing. For periodically occurring events, such as the cardiac and ventilatory cycle, the mapping point cloud may be a function of, or correlated to account for these factors. For instance, timing signals can be filtered and/or matched to images taken at corresponding signals/timings. In an embodiment, each mapping point may include additional parameters that indicate the conditions under which the point was recorded. Multiple mapping point clouds may then be assembled by grouping points together that were recorded under similar conditions. By monitoring the same or related factors during the real-time procedure, the system may choose the point cloud that most closely resembles the current conditions (e.g., using a lookup table). For example, FIGS. 12a and 12b represent two mapping point clouds 400, 402 that were recorded at different points within the sinus rhythm. As shown in the two figures, the ultrasound image illustrates that the cardiac tissue 404 has moved from a first position $R_1$ to a second, more contracted position $R_2$. By monitoring the subject's current electrocardiogram, they system may choose and/or modify the point cloud to more accurately reflect the current conditions of the heart, and may help to avoid erroneously overlaying mapping points. In an embodiment, compensation algorithms may be used to interpolate between various point clouds.

In an embodiment where the point cloud is a function of external factors, if desired the confidence evaluation and model adjustment may be performed on each distinct mapping point subset, such as shown in FIGS. 12a and 12b. In an embodiment, if the model is manipulated at one point in the cardiac phase, the system may extrapolate the modification to model sets at previous and/or subsequent times within the rhythm.

While numerous embodiments of this disclosure have been described above with a certain degree of particularity, those skilled in the art could make numerous alterations to the disclosed embodiments without departing from the spirit or scope of the invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed:

1. A method of refining an anatomical model existing in a three-dimensional model space, the method comprising:
   acquiring, from an ultrasound imager, a two-dimensional echocardiogram of an anatomical region of a patient having a plurality of pixels, each pixel associated with a respective intensity;
   relating, by a processor, the pixels of the two-dimensional echocardiogram to a plurality of mapping points, the mapping points existing in the three-dimensional model space, the mapping points representative of the anatomical region of the patient and derived from a position detection system;
   determining, by the processor, a confidence value for at least one of the mapping points according to the respective intensities of one or more of the plurality of pixels corresponding to the at least one mapping point;
   altering the anatomical model according to at least one of the confidence values; and
   displaying a representation of the altered anatomical model.

2. The method of claim 1, further comprising lowering the confidence value for the at least one of the mapping points based on an abnormality in the two-dimensional echocardiogram located proximate the at least one of the mapping points.

3. The method of claim 1, wherein:
   a set of the plurality of mapping points defines the three-dimensional model within the three-dimensional model space; and
   the confidence provides a measure of certainty as to whether at least one of the mapping points lies on a tissue boundary.

4. The method of claim 3, wherein the at least one mapping point does not belong to the model set, the method further comprising:
   comparing the confidence value to a threshold; and
   adding the at least one mapping point to the model set if the confidence value is above the threshold.

5. The method of claim 1, further comprising displaying the at least one mapping point with a visual attribute that corresponds to the determined confidence value for that point.

6. The method of claim 5, wherein the visual attribute is a color selected from a spectrum that corresponds to a range of confidence values.

7. The method of claim 5, wherein the visual attribute is a symbol that represents a range of confidence values.

8. The method of claim 1, wherein the two-dimensional echocardiogram is acquired from an ultrasound transducer associated with a distal portion of a catheter.

9. The method of claim 8, wherein relating the pixels of the two-dimensional echocardiogram to a plurality of mapping points comprises:
   receiving an indication of the position and orientation of the ultrasound transducer; and
   locating the pixels of the two-dimensional echocardiogram within the three-dimensional model space using the position and orientation of the ultrasound transducer.

10. The method of claim 9, wherein the indication of the position and orientation of the ultrasound transducer is received from a sensor associated with the distal portion of the catheter.

11. The method of claim 9, further comprising:
    displaying a representation of the two dimensional echocardiogram within the three-dimensional model space;
    determining the existence of an intensity gradient associated with the plurality of pixels; and
    identifying a boundary between blood and cardiac tissue based on the existence of the intensity gradient.

12. The method of claim 9, wherein a set of the mapping points defines the three-dimensional model within the three-dimensional model space; and
    wherein relating the pixels of the two-dimensional echocardiogram to a plurality of mapping points comprises:
    extracting boundary information from the model that is coincident with the plane of the two-dimensional echocardiogram; and
    overlaying the extracted boundary information on a representation of the two-dimensional echocardiogram.

13. The method of claim 9, wherein relating the pixels of the two-dimensional echocardiogram to a plurality of mapping points further comprises generating a three-dimensional echocardiogram intensity model within the three-dimensional model space.

14. The method of claim 13, wherein the three-dimensional echocardiogram intensity model comprises a plurality of voxels, each voxel having an intensity relating to an intensity of a portion of one or more acquired two-dimensional echocardiograms.

15. The method of claim 13, wherein the three-dimensional echocardiogram intensity model is updated for a successively acquired two-dimensional echocardiogram.

16. A system for assessing an accuracy of an anatomical model, the anatomical model existing in a three-dimensional model space, the system comprising:

an ultrasound echo imaging system configured to acquire a two-dimensional echocardiogram of an anatomical region of a patient having a plurality of pixels, each pixel associated with a respective intensity;

a database having stored therein a plurality of mapping points existing in the three-dimensional model space, the mapping points representative of the anatomical region of the patient and derived from a position detection system; and a processor configured to:

relate the pixels of the two-dimensional echocardiogram to the plurality of mapping points;

determine a confidence value for at least one of the mapping points according to the respective intensities of one or more of the pixels corresponding to the at least one mapping point; and assess the accuracy of the anatomical model according to the confidence value.

17. The system of claim 16, wherein the processor is further configured to display an augmented echo image including a representation of the two-dimensional echocardiogram and one or more mapping points, each of the one or more displayed mapping points having a visual attribute corresponding to a respective confidence value.

18. The system of claim 16, wherein relating the pixels of the two-dimensional echocardiogram to a plurality of mapping points includes generating a three-dimensional ultrasound model from the two-dimensional echocardiogram.

19. The system of claim 16, wherein a set of the mapping points defines the anatomical model.

20. The system of claim 19, wherein the processor is further configured to compare the confidence value to a threshold and modify the set of mapping points if the confidence value exceeds the threshold.

* * * * *